March 29, 1949. J. J. GRULLEMANS Plant Pat. 830
CYDONIA PLANT
Filed July 21, 1947
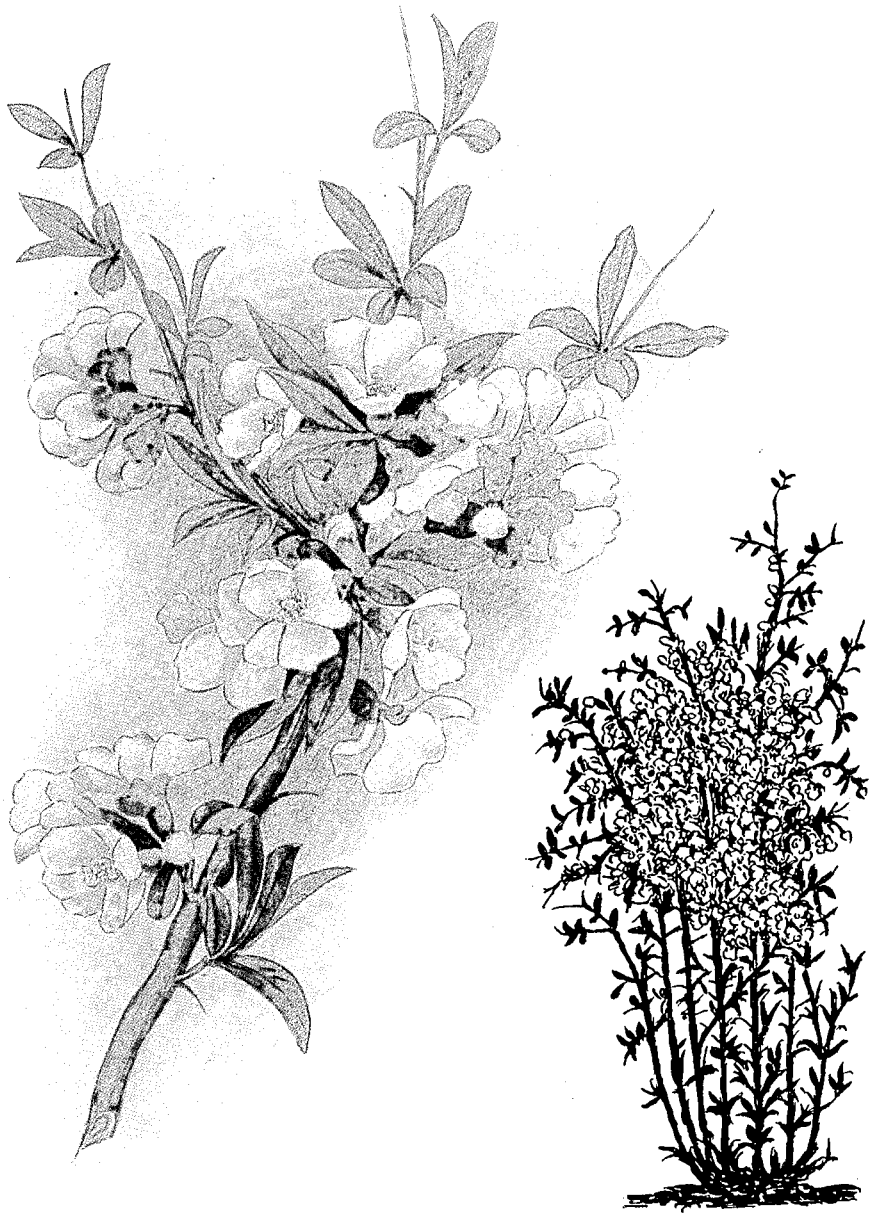
WITNESS
Addison J. Avery
INVENTOR
John J. Grullemans,
by: John H. Leonard,
his ATTY Patented Mar. 29, 1949

Plant Pat. 830

UNITED STATES PATENT OFFICE

830

CYDONIA PLANT

John J. Grullemans, Painesville, Ohio

Application July 21, 1947, Serial No. 762,487

1 Claim. (Cl. 47—60)

This invention relates to a new and distinct variety of cydonia plant, commonly termed flowering quince.

The new variety is illustrated in the drawing in which the colored figure shows a terminal of a main stalk as it appears when the plant is in bloom and the black and white figure illustrates the columnar shape and open appearance of the plant, the blossoms being omitted from the lower portion of the plant for clearness in illustrating the arrangement of the main stalks.

The present hybrid plant was obtained by first crossing two hybrid cydonia japonica plants. Seeds from this cross were planted and the resulting plants were crossed again. Seeds from the second crossing were planted and one of them produced the present cydonia plant.

The plant was developed and first grown by me in Lake County, Ohio, and was asexually reproduced by me from hardwood cuttings.

The root structure of the plant is rather openly branched for this type of plant, the roots being of the usual size and quite deep but having a greater lateral spread than is usual. The root structure has the usual hardiness and resistance to wetness and drouth and has the usual winter resistance, both protected and unprotected, having withstood temperatures considerably below zero unprotected in northern Ohio. The plant is rather indifferent as to types of soils.

The exposed plant structure is the usual woody shrub but instead of being open and sprawling in shape as is common to cydonia plants, the main stalks are exceedingly upright from the ground to the crown of the plant and the laterals are comparatively short and sparse except near the crown, thus giving the bush a narrow columnar shape and also exposing much better than in the usual type of cydonia plant the large number of blooms along the stalks. The main stalks from just below the crown to a distance of about six inches to a foot above the ground are masses of well exposed blooms interspersed with a few green leaves, yet the crown portion has and exposes as many blooms as do other varieties of cydonia plants.

In a number of four year old plants examined carefully there are about six or seven main stalks to a plant, the main stalks averaging about five to six feet in length. These stalks grow generally parallel to each other and are spaced apart a few inches just above the ground. The lateral spread of the plants at the crown averages from two to three feet, whereas in other varieties of about the same age and growing under the same conditions the lateral spread is from three to four feet and, in the latter, the stalks start their divergence just above the ground and the laterals are much longer than in the present plant.

The resistance of the exposed plant to low temperature, disease, drouth and wetness is about the usual resistance for cydonia plants. The present plant is a very vigorous grower. It prefers full sun but does well in partial shade and is indifferent to exposure. It prefers a well drained garden loam.

The main stalks have the usual surface texture and, as mentioned, grow generally parallel directly from the roots. The branches are of the usual alternate arrangement with a tendency toward a whorled arrangement. They have relatively smooth bark.

The leaves are arranged openly. They are generally whorled, as is usual with cydonia plants. The new leaves are green comparable to Maerz and Paul Plate 20–L–7, a number of the leaves being touched with a color comparable to Maerz and Paul Plate 14–L–8. Generally, they are best described as green edged with a reddish brown. They are of the usual size and shape and of average thickness. They have a smooth glossy texture. Their persistency on the plant is excellent. The petioles are strong.

The plant grows and blooms well throughout the United States. For an abundance of blooms exposures other than north are preferred. The best blooms appear to be obtained in a rich loam acid soil. The number of blooms is little affected by conditions of sun, shade, moisture, heat or cold but the size of the blooms is considerably reduced in dry seasons. The blooming period extends through May and the first week of June and during this period the plant blooms continuously. The buds are very large, being about one and one half times the average for cydonia plants. They are generally oval in shape and arranged in the usual whorled position on the stalks and branches. The individual blossoms average from one and one quarter to one and one half inches in diameter and grow in the usual clusters. Their permanence on the growing plant is good as also is their permanence when cut. The lightest color of the blossoms is comparable to Maerz and Paul Plate 1–J–9, shading into a color comparable to Maerz and Paul Plate 2–L–8, and this in turn shading into hues as dark as Maerz and Paul Plate 3–L–6. The same is true of the buds.

The calyx of a bud is usually a green comparable to Maerz and Paul Plate 18–K–6 and the rounded ends thereof are tipped with a color comparable to Maerz and Paul Plate 6–L–3. The pistils are of a color comparable to Maerz and Paul Plate 12–L–1 and the stamens compare with Maerz and Paul Plate 10–K–6. The stalks compare in color to Maerz and Paul Plate 15–L–9, with thorns sparsely distributed and comparable in color to Maerz and Paul Plate 16–A–12. The general tonality of the plant from a distance when in full bloom is comparable to Maerz and Paul Plate 2–L–10.

The color of the blooms is quite permanent, there being no noticeable change during the blooming season. The petals are smooth and velvety in texture and their form and arrangement is usual. The general shape of the flower is usual except for its size.

The characteristics which distinguish the present cydonia plant from other varieties are its extremely upright columnar growth, the large size of its individual buds and blooms, and the limited number of short lateral branches which expose the blooms well substantially from the crown to the ground, thus providing a cydonia plant which is suitable for hedges and the like for which the usual cydonia plants are unsuitable due to their sprawling nature.

Having fully shown and described my cydonia plant and its mode of asexual reproduction, I claim:

The variety of cydonia plant herein shown and described characterized by its upright columnar growth, the large size and attractive color of its buds and blossoms and its relatively sparse and short lateral branches which expose the blossoms well from the crown subtantially to the ground.

JOHN J. GRULLEMANS.

No references cited.